United States Patent [19]

Cox

[11] Patent Number: 4,754,746
[45] Date of Patent: Jul. 5, 1988

[54] SELF-RETAINING METATARSAL SPREADER

[76] Inventor: Kenneth L. Cox, 1653 Medical Dental Bldg., Seattle, Wash. 98101

[21] Appl. No.: 911,570

[22] Filed: Sep. 25, 1986

[51] Int. Cl.$^4$ ............................................. A61B 17/02
[52] U.S. Cl. ........................................ 128/20; 128/17; 81/302
[58] Field of Search ........................ 128/17, 19, 20, 81, 128/18, 84 R, 89 R, 321, 322, 346, 303 R; 81/302; 29/239; 433/7, 157, 159, 148, 149

[56] References Cited

U.S. PATENT DOCUMENTS

| | | | |
|---|---|---|---|
| 390,561 | 10/1888 | Brown | 433/159 |
| 569,839 | 10/1896 | Roeloffs | |
| 835,968 | 11/1906 | Mennes | |
| 1,305,749 | 6/1919 | Shirley | |
| 2,217,968 | 10/1940 | Radcliff | 128/345 |
| 2,643,565 | 6/1953 | Mount | 81/302 |
| 2,757,666 | 8/1956 | Grant | 81/302 |
| 3,038,467 | 6/1962 | Sovatkin | 128/17 |
| 3,470,872 | 10/1969 | Grieshaber | 128/17 |
| 3,766,910 | 10/1973 | Lake | 122/20 |
| 4,034,746 | 7/1977 | Williams | 128/17 |
| 4,165,746 | 8/1979 | Burgin | 128/321 |

FOREIGN PATENT DOCUMENTS

| | | | |
|---|---|---|---|
| 350214 | 11/1905 | France | 128/20 |
| 358930 | 3/1906 | France | 128/17 |
| 333 | of 1897 | United Kingdom | 128/17 |

OTHER PUBLICATIONS

*Chicago Medical Equipment Company* Catalog, Northbrook, Ill., 1984, p. 69, Item No. 586 and Item No. 5378.
Loose leaf catalog distributed by Zimmer, USA, Warsaw, Ind., Jun. 1978, p. D44.

Primary Examiner—Richard C. Pinkham
Assistant Examiner—Mark S. Graham
Attorney, Agent, or Firm—Ward Brown; Robert W. Beach

[57] ABSTRACT

Opposing jaws of a retractor are pivoted together and extend oppositely from handles manually swingable to move the jaws relatively toward and away from each other. Generally rectangular blades extend downward from the swinging ends of the jaws and have planar leading bottom portions contiguously engageable for fitting between closely adjacent bone such as metatarsals. The trailing portions of the blades are flared outward and rearward from the planar contiguously engageable portions for wedging the adjacent bones apart and have concave depressions for receiving the bones. With the bones received in the concave depressions, the jaws are swung apart to spread the bones and maintain them in spread-apart condition for convenient access to the facing surfaces of the bones, such as to excise a neuroma.

4 Claims, 2 Drawing Sheets

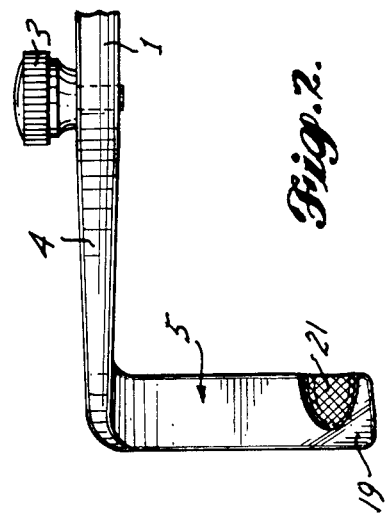
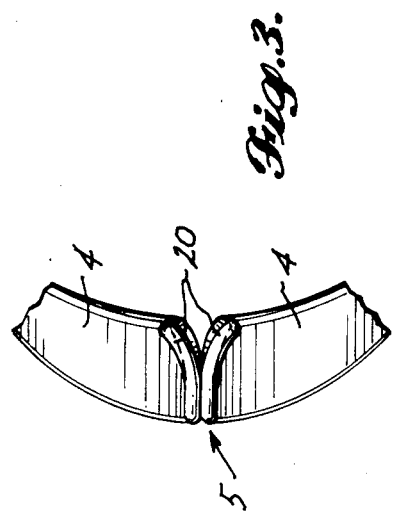
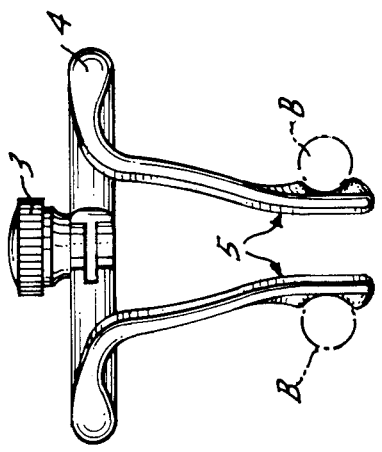
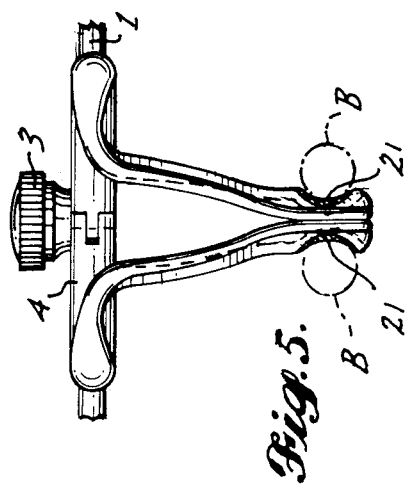
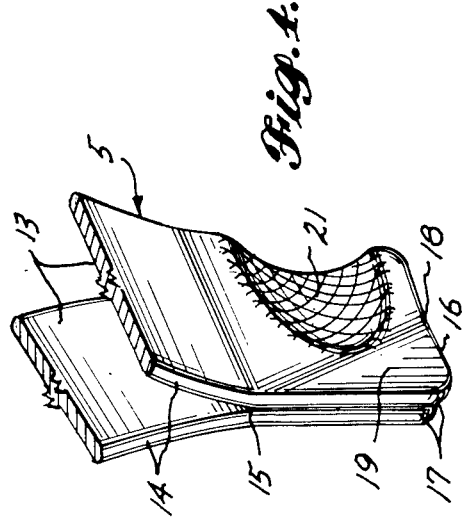

SELF-RETAINING METATARSAL SPREADER

BACKGROUND OF THE INVENTION

1. Field of the Invention

The present invention relates to a medical instrument for spreading apart adjacent body parts of a patient during surgery. The disclosed embodiment is specifically designed for spreading apart and maintaining in spread-apart condition adjacent metatarsals for convenient access by a foot surgeon.

2. Prior Art

A fairly common affliction of the foot is development of a painful neuroma close to or between the heads of adjacent metatarsals, such as along the third common digital nerve in the area of the transverse metatarsal ligament where such nerve curves plantarward. Treatment can be by surgical excision of the neuroma. It is important to excise the neuroma completely, but access to the affected area can be limited by the closely spaced bones and the ligament itself.

There is no known instrument designed specifically for spreading apart and retaining in spread-apart condition the adjacent metatarsals, but instruments designed primarily for other purposes have been used. Retractors having long handles and more or less hooked ends can be fitted between the adjacent bones and pulled apart manually by a surgical assistant. Clever surgeons have tried flattening the blades of known retractors with pivoted opposing jaws, but the flattened blades can be difficult to insert between the metatarsals and can slip or even pop out from between the bones.

SUMMARY OF THE INVENTION

The principal object of the present invention is to provide a medical instrument effective for spreading apart and maintaining in spread-apart condition adjacent bones of a patient, particularly adjacent metatarsals, enabling access to the opposing faces for excision of a neuroma, which instrument is of simple, inexpensive construction and easy to use, and which will reliably maintain the bones in spread-apart condition without requiring additional attention of the surgeon or a surgical assistant.

In the preferred embodiment of the present invention, the foregoing object is accomplished by a pivoted retractor of generally conventional construction in that the retractor has the usual pivoted handles and jaws with manually releasable ratchet mechanism for normally maintaining downward-projecting blades in progressively greater spread-apart positions as the handles are squeezed together, but with blades of novel design. In the preferred embodiment, the blades have flat, contiguously engaged, lower forward corner portions such that, with the instrument inclined downward and forward, such tips will fit easily between adjacent bones. The lower rear portions of the blades are flared outward so that, as the instrument is subsequently moved to a horizontal position, the adjacent bones are wedged apart slightly until they fit in concave depressions at the trailing edge portions of the blades. The bones are reliably maintained in the depressions as the jaws of the instrument are spread apart.

BRIEF DESCRIPTION OF THE DRAWINGS

FIG. 2 is a fragmentary side elevation of the leading end portion of the self-retaining metatarsal spreader shown in FIG. 1, on a larger scale.

FIG. 3 is a fragmentary bottom plan of the leading end portion of the self-retaining metatarsal spreader of FIG. 1, on a larger scale than FIG. 2.

FIG. 4 is a fragmentary top perspective of the bottom portions of the blades of the self-retaining metatarsal spreader of FIG. 1, on a still larger scale.

FIGS. 5 and 6 are corresponding front end elevations of the self-retaining metatarsal spreader of FIG. 1 with parts in different positions, on the same scale as FIG. 2 and with the spreader handles deleted.

DETAILED DESCRIPTION

Figure 1:
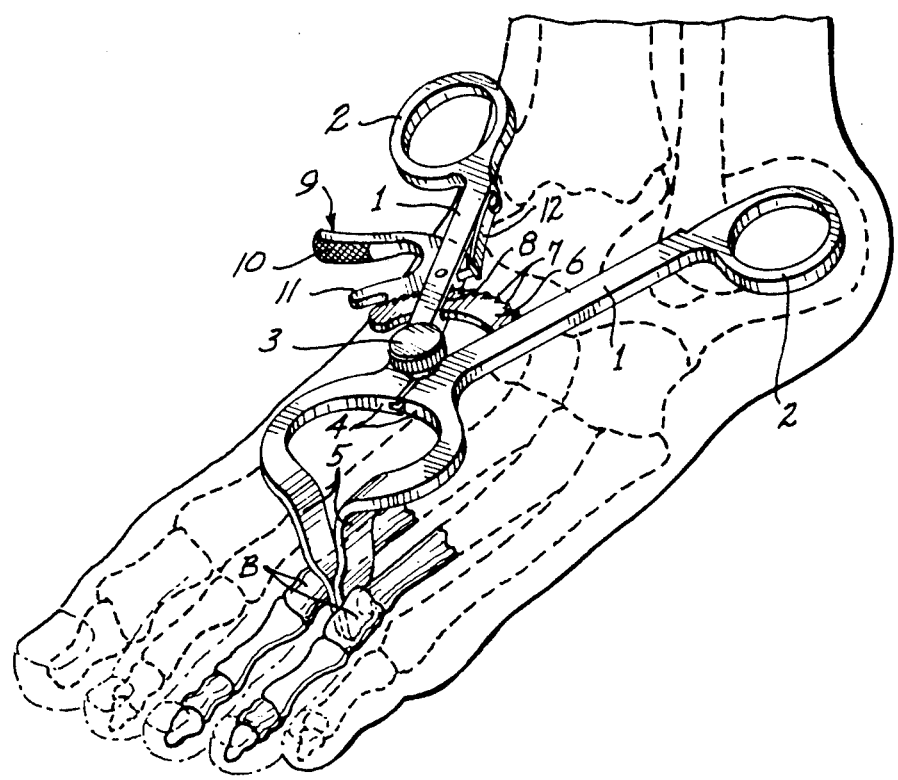
FIG. 1 is a somewhat diagrammatic top perspective of a self-retaining metatarsal spreader in accordance with the present invention, showing the foot of a patient partially in phantom with the downward-projecting blades of the spreader inserted between adjacent metatarsals.

As shown in FIG. 1, the self-retaining metatarsal spreader in accordance with the present invention resembles a conventional pivoted retractor with opposing elongated handles 1. Each elongated handle has an end finger ring 2. The handles are connected by the central pivot pin or screw 3. Integral with the handles are opposing arcuate jaws 4 preferably coplanar with the long and straight handles 1. The bone-spreading blades 5, described in detail below, extend downward from the leading or distal ends of the jaws 4.

An arcuate ratchet segment 6 with closely spaced teeth 7 extends inward from one of the handles 1 through a slot 8 in the other handle. Such segment cooperates with a pawl member 9 pivotally mounted in another slot through such other handle closely adjacent to the slot 8. The pawl member has teeth complementary to the ratchet segment teeth 7. The pawl member has an outward-projecting actuating finger 10 and, preferably, another finger 11 spaced forward from finger 10 to protect the finger of the user from cutting or pinching engagement against the ratchet teeth 7, similar to the instrument described in U.S. Pat. No. 3,038,467. A cantilever leaf spring 12 extends along the inner side of the same handle to which the pawl mechanism 9 is pivoted. Preferably, the leaf spring cooperates with an inner arcuate abutment or cam of the pawl member in over center manner to bias the pawl member to the engaged position shown in FIG. 1 or optionally retain it in a released, disengaged position.

In the position shown in FIG. 1, squeezing the handles 1 together results in spreading the jaws 4 and their blades 5 apart so as to spread the metatarsals B between which the blades 5 are inserted. This permits convenient access to the facing sides of the metatarsals, such as to excise a neuroma. Even greater access is accomplished by the arcuate shape of each jaw 4 which leaves the wide, generally circular area between the facing sides of the jaws, so as not to obstruct access to the bones.

As seen in FIG. 2, in profile each blade 5 is generally rectangular, of substantially uniform width from top to bottom. With reference to FIG. 4, the upper portions 13 of the blades are inclined downward and inward toward each other until the leading edges 14 of the blades meet at a point 15 approximately one-quarter to one-third of the total length of each blade from the blade bottoms 16. From such meeting point 15 the thin leading edges 14 of the blades are in substantially contiguous engagement down to the rounded lower forward corners 17. From such corners, the blade bottom edges remain in substantial contiguous engagement to a point 18 at about the midpoint of the width of the blades. As illustrated by the shading of FIGS. 2 and 4, each blade has a planar lower forward corner portion 19 of generally right-triangular shape, contiguously engageable against the corresponding lower forward corner portion of the other blade. Consequently, with the spreader handles and jaws tilted downward and forward, such corner portions 19 can be easily fitted between even closely adjacent bones.

As seen in FIGS. 3 and 4, from the planar, contiguously engageable corner portions 19, the blades 5 are flared apart rearward, that is, as seen in FIG. 3, the trailing portion 20 of the lower portion of each blade is gently curved outward to its rear edge. In the flared trailing portion 20 of each blade, a concave depression 21 is formed immediately behind the planar lower forward portion 19. The bases or center lines of the depressions extend horizontally and, in the closed positions of the blades, the bases or center lines are flared slightly rearward.

After tilting of the spreader and insertion of the contiguously engaged lower forward portions 19 between adjacent bones, the spreader can be swung back toward a horizontal position while maintaining downward pressure so that the flared trailing portions of the blades fit between bones or gently wedge them apart. The bones B will fit in the depressions 21 as seen, for example, in FIG. 5. FIG. 6 shows a slightly exaggerated spread-apart position of the bones. It will be noted that, with the blades 5 in the desired spread-apart positions, the bases of the depressions are substantially parallel, whereas the flat lower forward corner portions of the blades are flared forward and outward slightly. At any rate, the bones are reliably retained in the concave depressions 21 which preferably have criss-crossed grooves or ribs to bite into tissue surrounding the bones and thereby prevent slippage.

In the preferred embodiment, each blade can be formed from stainless steel stock and be about 32 millimeters high by about 8 millimeters wide and about 2 millimeters thick. Consequently, the double-blade thickness of the contiguously engaged lower forward portions 19 presented between adjacent bones is only about 4 millimeters. The trailing portion of each blade can flare outward about 5 to 8 millimeters and each depression 21 should be at least 2 millimeters deep, preferably about 3 millimeters deep. The center lines of the depressions can be spaced upward from the blade bottoms about 5 millimeters.

Preferably the generally right triangular planar portions 19 of the blades have perpendicular base edges at least about 4 millimeters long for easy retention of such portions between closely adjacent bones as the spreader is tilted toward a horizontal position while wedging such bones apart.

In an adult patient, the handles 1 rest conveniently on the top of the patient's foot unobtrusively, making it less likely that the blades will be dislodged by the surgeon or an assistant during surgery.

I claim:

1. Mechanism for spreading apart adjacent bones of a patient comprising a pair of adjacent upright blades each having respective leading and trailing bottom portions, said leading bottom portions of said blades being planar and contiguously engageable for fitting between the adjacent bones and said trailing bottom portions of said blades including portions flared relatively outward and rearward from said leading bottom portions, at least one of said blades having a depression in its flared trailing portion, the greatest depth of said depression being spaced upward from the bottom edge of its blade and said depression forming an outturned projection at the bottom of such blade below the greatest depth of said depression for receiving and holding one of the adjacent bones, and means for moving said blades relatively apart so as to spread apart said bones when said blades are fitted between said bones with one of said bones received in said depression.

2. Mechanism for spreading apart adjacent, generally parallel, horizontal metatarsals of a patient comprising a pivoted retractor having opposing horizontal jaws and generally rectangular blades extending downward from corresponding swinging ends of said jaws, said blades having respective top and bottom portions and respective leading and trailing portions, the leading bottom corner portions of said blades being planar and contiguously engageable for fitting between the adjacent metatarsals with said blades tilted relative to said metatarsals, the trailing bottom portions of said blades being flared outward from their respective leading forward portions, said planar leading bottom corner portions of said blades being of generally right-triangular shape including perpendicular base edges along the leading and bottom edges of the blade, respectively, each of said trailing bottom portions of said blades having a concave depression for receiving the convex adjacent side of the adjacent metatarsal when said blades are fitted between said metatarsals, and means for moving said jaws so as to move said blades relatively apart while said adjacent metatarsals are received in said depressions.

3. Mechanism for spreading apart adjacent, generally parallel, horizontal metatarsals of a patient comprising a pivoted retractor having opposing horizontal jaws and generally rectangular blades extending downward from corresponding swinging edges of said jaws, said blades having respective top and bottom portions and respective leading and trailing portions, the leading bottom corner portions of said blades being planar and contiguously engageable for fitting between the adjacent metatarsals with said blades tilted relative to said metatarsals, the trailing bottom portions of said blades being flared outward from their respective planar leading forward portions, each of said trailing bottom portions of said blades having a concave depression for receiving the convex adjacent side of the adjacent metatarsal when said blades are fitted between said metatarsals, said depression forming an outturned projection at the bottom of such blade below the greatest depth of said depression each of said depressions having a center line about which such depression is substantially symmetrical and said center lines of said depressions being coplanar and flared outward and rearward relative to each other when the blades have their planar leading bottom corner portions engaged.

4. Mechanism for spreading apart adjacent, generally parallel, horizontal metatarsals of a patient comprising a pivoted retractor having opposing horizontal jaws and generally rectangular blades extending downward from corresponding swinging ends of said jaws, said blades having respective top and bottom portions and respective leading and trailing portions, the leading bottom corner portions of said blades being planar and contiguously engageable for fitting between the adjacent metatarsals with said blades tilted relative to said metatarsals, the bottom edge of said planar leading bottom corner portion of each blade extending rearward to about midway between the leading and trailing edges of such blade and the trailing bottom portions of said blades being flared outward from their respective planar leading forward portions from about midway between the leading and trailing ends of said blades, each of said trailing bottom portions of said blades having a concave depression for receiving the convex adjacent side of the adjacent metatarsal when said blades are fitted between said metatarsals, the greatest depth of each of said depression being spaced upward from the bottom of its blade forming an outturned projection at the bottom of such blade below the greatest depth of said depression, and means for moving said jaws so as to move said blades relatively apart while said adjacent metatarsals are received in said depressions.

* * * * *